United States Patent
Lin et al.

(10) Patent No.: US 7,679,749 B2
(45) Date of Patent: Mar. 16, 2010

(54) OPTICAL WAVEGUIDE SURFACE PLASMON RESONANCE SENSOR

(75) Inventors: Chii-Wann Lin, Taipei (TW);
Jheng-Long Lee, Taipei (TW);
Rong-Huay Juang, Taipei (TW);
Shi-Ming Lin, Taipei (TW); Chih-Kung Lee, Taipei (TW); Rea-Min Chu, Taipei (TW); Ching-Ho Wang, Taipei (TW);
Jim-Min Fang, Taipei (TW);
Tsung-Liang Chuang, Taipei (TW)

(73) Assignee: Council of Agriculture, Executive Yuan, Taipei (TW)

( * ) Notice: Subject to any disclaimer, the term of this patent is extended or adjusted under 35 U.S.C. 154(b) by 167 days.

(21) Appl. No.: 12/076,203

(22) Filed: Mar. 14, 2008

(65) Prior Publication Data

US 2009/0073420 A1 Mar. 19, 2009

(30) Foreign Application Priority Data

Sep. 14, 2007 (TW) ............................. 96134557 A (51) Int. Cl.
*G01N 21/55* (2006.01)
(52) U.S. Cl. .................................................. 356/445
(58) Field of Classification Search .................. 356/445
See application file for complete search history.

(56) References Cited

U.S. PATENT DOCUMENTS 6,330,064 B1 * 12/2001 Rieder ........................ 356/481

OTHER PUBLICATIONS

Ohmori et al., "Organic electroluminescent diodes as a light source for polymeric waveguides—toward organic integrated optical devices", Elsevier Science B .V., 2001,pp. 267-272.
Dostalek et al, "Surface plasmon resonance biosensor based on integrated optical waveguide"Elsevier Science B.V., 2001, pp. 8-12.
McDonnell, "Surface plasmon resonance: towards an understanding of the mechanisms of biological molecular recognition" Current Opinion in Chemical Biology, 2001, pp. 572-577, vol. 5.
Harris et al., "Integrated optical surface plasmon resonance immunoprobe for simalzine detection", Biosensors & Bioelectronics, 1999, pp. 377-386, vol. 14.

* cited by examiner

*Primary Examiner*—F. L Evans
(74) *Attorney, Agent, or Firm*—Birch, Stewart, Kolasch & Birch, LLP (57) ABSTRACT

An optical waveguide SPR sensor is adapted for differential measurement. The optical waveguide SPR sensor includes a base, a bottom layer, and at least one set of optical waveguide layers. The set of the optical waveguide layers includes a measuring optical waveguide channel and a reference optical waveguide channel. The measuring optical waveguide channel includes an SPR sensing film layer. The measuring optical waveguide channel and the reference optical waveguide channel are independently configured and substantially parallel one to another. The bottom layer has a refractive index higher than a refractive index of the optical waveguide layer.

23 Claims, 6 Drawing Sheets

OPTICAL WAVEGUIDE SURFACE PLASMON RESONANCE SENSOR

BACKGROUND OF THE INVENTION

1. Field of the Invention

The present invention relates to a surface plasmon resonance (SPR) sensor, and in particular, to an optical waveguide SPR sensor.

2. The Prior Arts

Physiological phenomenon of organisms often includes many very complicated biochemical reaction mechanisms. Such biochemical reaction mechanisms often involve interactions of macromolecules with other molecules. Therefore, many analysis methods and tools are provided to detect the reactions of the macromolecules for the purpose of understanding such complex reaction mechanisms.

Among so many analysis methods and tools, biosensors based on surface plasmon resonance (SPR biosensor) gradually attract more attention. Since 1990, there have been many manufactures producing the SPR biosensors. The manufacturers are listed in table 1 recited below, given by McDonnell, Chemical Biology (2001) 5:572-577.

TABLE 1

Manufactures of SPR Sensors

| Manufactures and their Websites | Product |
| --- | --- |
| BIAcore AB (Uppsala, Sweden) http://www.biacore.com | BIAcore |
| Affinity Sensors (Franklin, MA) http://www.affinity-sensors.com | IASys |
| Nippon Laser Electronics (Hokkaido, Japan) http://www.rikei.com | SPR-670 |
| Artificial Sensing Instruments (Zurich, Switzerland) http://www.microvacuum.com/products/biosensor | OWLS |
| IBIS Technologies BV (Enschede, The Netherlands) http://www.ibis-spr.nl | IBIS |
| Texas Instruments (Dallas, TX) http://www.ti.com/spreeta | TISPR |
| Aviv (Lakewood, NJ) http://www.avivinst.com | PWR-400 |
| BioTul AG (Munich, Germany) http://www.biotul.com | Kinomics |
| Quantech Ltd (Eagan, MN) http://www.quantechltd.com | FasTraQ |

In general, SPR biosensors have the advantages of high sensitivity, labeling free to the analyte, fast testing, and adapted for real-time analysis of interactions between molecules, quantitative analysis, and mass parallel screening. They are also practically applied to detect intermolecular reactions between, for example, antigens and antibodies, enzyme and its substrate, hormone and its receptor, as well as nucleic acid and nucleic acid. An SPR biosensor can also be incorporated with a biochip to set up a new drug screening platform. Further, a sensor based on SPR is also applicable for analytical chemistry, environmental engineering, or even military purpose.

The underlying physical principle of SPR is that when a light beam incident to a surface of a metal film with a certain incident angle, an intensity of reflected light beam detected by a light detector approaches zero. In other words, a reflectivity of the metal film approximates to zero. The unreflected light becomes an evanescent wave, and is transmitted along a direction parallel with the interface with a certain speed. Such an evanescent wave excites an SPR at the surface of metal film, and the phenomenon is known as an attenuated total reflection (ATR).

A conventional SPR sensor conducts measurements according to the foregoing principle. Such a conventional SPR sensor usually includes a thin metal layer and a sensing region adjacent to the thin metal layer. The thin metal layer is often configured on a dielectric prism or grating. The dielectric prism or grating is used as an optical coupler for exciting SPR. With such a conventional SPR sensor is operated to measure an analyte, the analyte is carried through the sensing region, and a light beam is incident the prism or the grating and arrives a surface of the thin metal layer. An intensity of reflected light at the surface of the thin metal layer is measured. As the matter sensed at the sensing region of the SPR sensor changes, correspondingly detected SPR characteristics also change. In this manner, interactions between different matters or concentration of a certain matter can be measured by measuring the certain angle at which the light reflectivity sharply attenuates.

However, the foregoing SPR sensor measures mainly by modulating the incident angle of the incident light and measuring a corresponding intensity change of the reflected light, so that the resolution and sensitivity thereof are restricted by the angle range of the incident light which excites the SPR. In another hand, the incident angle of the incident light for exciting the SPR is also related to a wavelength thereof. As such, when the wavelength varies, it causes errors of the measurement.

Another typical SPR utilizes optical waveguide as the optical coupler. This SPR sensor includes a thin metal layer and a sensing region adjacent to the thin metal layer. The thin metal layer is configured on an optical waveguide. After incident in the optical waveguide, when a component of the wave vector of the incident light at a direction parallel with the interface equals to a wave vector of a surface plasmon wave, an SPR is then excited, and thus causing a light intensity attenuation at an output end of the optical waveguide. Dielectric indices of respectively the analyte and the thin metal layer determine the wave vector of the surface plasmon wave, and therefore, when the analyte varies, the dielectric index thereof changes correspondingly. As such, interactions between different matters or concentration of a specific matter can be measured by measuring a characteristic wavelength or an attenuation of light intensity when SPR occurs.

The optical waveguide SPR sensor is usually adapted for two measurement modes for measuring analyte. The first mode is utilizing a light source of a specific wavelength and measuring an attenuation of the light intensity. The second mode is utilizing a white light having a continuous wave frequency spectrum to measure a characteristic wavelength of which a light intensity sharply attenuates. As such, the resolution and sensitivity of the optical waveguide SPR sensor are not restricted by the range of the incident angle of the incident light at which the SPR is excited. Further, the optical waveguide SPR sensor is convenient for integration which requires only a little sample for precision measurement, and thus is more applicable.

A conventional optical waveguide SPR sensor has been disclosed by Yutaka Ohmori et al., Thin Solid Films, 393, 267-272, 2001, and J. Dostalek et al., Sensors and Actuators B, 76, 8-12, 2001. This optical waveguide SPR sensor is configured by a method including: disposing a metal film having a waveguide pattern on a substrate by an optical etching or a coating process; and then implementing ions to the substrate by a high temperature ion exchanging process to change the refractive index of the substrate, and thus obtaining an optical waveguide. In order to attaining the SPR, a metal layer and a dielectric layer used for adjusting a sensing range are further required to be disposed on the waveguide by a semiconductor processing as a SPR sensing region. This conventional optical waveguide SPR sensor is generally a single channel optical waveguide SPR sensor, which has only sensing region on the optical waveguide. As such, it is incapable of providing a multi-sample measurement or a reference differential measurement. Therefore, errors of the measurement result obtained by this conventional optical waveguide SPR sensor are still relatively large.

Furthermore, another optical waveguide SPR sensor is proposed by R. D. Harris et al., Biosensors & Bioelectronics 14 (1999) 377-386. Although this optical waveguide SPR sensor includes a reference arm, the optical waveguide is designed as Y-shape bifurcated. Unfortunately, this causes uneven light distribution and unwanted light attenuation, which are difficult to overcome in considering the processing precision and cost.

SUMMARY OF THE INVENTION

An objective of the present invention is to provide an optical waveguide SPR sensor, adapted for a differential measurement. The optical waveguide SPR sensor includes a base, a bottom layer, and at least one set of optical waveguide layers. The set of optical waveguide layers includes a measuring optical waveguide channel and a reference optical waveguide channel. The measuring optical waveguide channel includes an SPR sensing film layer. The measuring optical waveguide channel and the reference optical waveguide channel are independently configured and substantially parallel one to another. The bottom layer has a refractive index higher than a refractive index of the optical waveguide layer.

The foregoing base can be made of a silicon wafer, a glass, or a macromolecule material. The bottom layer can be made of a photoresist material with a relatively high refractive index, silicon dioxide, silicon dioxide having germanium or boron doped therein, or macromolecule material, and the thickness thereof is preferably not less than 5 µm.

The foregoing optical waveguide can be made of a photoresist material with a relatively low refractive index, silicon dioxide, silicon dioxide having germanium or boron doped therein, or macromolecule material, and the thickness thereof is preferably not less than 10 µm. A distance between adjacent optical waveguide channels in the optical waveguide layer is from about 500 µm to about 5000 µm, and a width of the optical waveguide channel is from 20 µm to about 500 µm.

The foregoing SPR sensing film layer is preferably a film stack adapted for exciting a SPR when the incident light has a wavelength in a range of 400 to 1100 nm. The SPR sensing film layer for example can be a metal film, an alloy film, such as Au—Ag alloy film, or a film stack composed of a metal film and a plurality of dielectric films.

Further, the foregoing SPR sensing film layer may further include a biomolecule which can be combined with the analyte, e.g., nucleic acid, peptide, or protein, serving as a probe or a ligand molecule which is reactive with the analyte.

Further, the foregoing optical waveguide SPR sensor is preferably disposable.

Furthermore, the SPR sensor according to the present invention further includes a flow conducting structure layer, adapted to conduct the analyte to flow into the sensing film layer for measurement. According to one embodiment, the flow conducting structure layer for example can be a micrometer scale slot, e.g., a slot having a depth of 10 to 500 µm, or a side flow conducting structure made of a porous material, or a combination of these two structures. The analyte can be conducted into the sensing film layer by transmittance or diffusion along the slot structure by a capillary effect.

Preferably, a refractive index of the flow conducting structure layer is from about 1.33 to about 1.35.

The foregoing slot structure for example is made by a conventional microlithography process or an optical etching process which are capable of configuring micrometer scale slots.

According to an embodiment of the present invention, the flow conducting structure layer includes: a substrate, serving as a supporter supporting other structures; a filter film layer, disposed under the substrate for filtering and conducting a sample; a sample loading pad, disposed at an end of the flow conducting structure layer for loading the sample; and an absorption pad, disposed at another end of the flow conducting structure layer opposite to the sample loading pad for absorbing excessive sample. The filter film layer for example can be nitrocellulose or cellulose acetate.

According to another embodiment of the present invention, the flow conducting structure layer includes: a substrate, serving as a supporter supporting other structures; a micrometer scale slot structure, disposed at a side of the substrate facing the optical waveguide layer for conducting a sample therein; a sample loading pad, disposed at an end of the flow conducting structure layer for loading and filtering the sample; and an absorption pad, disposed at another end of the flow conducting structure layer opposite to the sample loading pad for absorbing excessive sample. The sample loading pad for example can include nitrocellulose or cellulose acetate for filtering the sample.

According to still another embodiment of the present invention, the flow conducting structure layer includes: a substrate, serving as a supporter; a micrometer scale slot structure, disposed under the substrate for conducting and filtering a sample; a sample loading pad, disposed at an end of the flow conducting structure layer for loading the sample; and an absorption pad, disposed at another end of the flow conducting structure layer opposite to the sample loading pad for absorbing excessive sample. The micrometer scale slot structure for example can include nitrocellulose or cellulose acetate for filtering the sample.

According to the foregoing embodiments, the present invention is adapted for more precision differential measurements by employing a measuring optical waveguide channel and a reference optical waveguide channel which are independent one from another and substantially parallel one to another. Further, the SPR sensor according to the present invention may includes a plurality of sets of sensing optical wave layers, so as to allow a single SPR waveguide sensor to measure a plurality of samples at the same time, which is distinct from the single measurement by the conventional SPR sensor. Moreover, the employment of the flow conducting structure layer of the micrometer scale slot or the side flow conducting structure made of a porous material enhances the applicability of further developing a high flux measurement of and a portable SPR sensor adapted for higher sensitivity.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

First Embodiment

Figure 1:
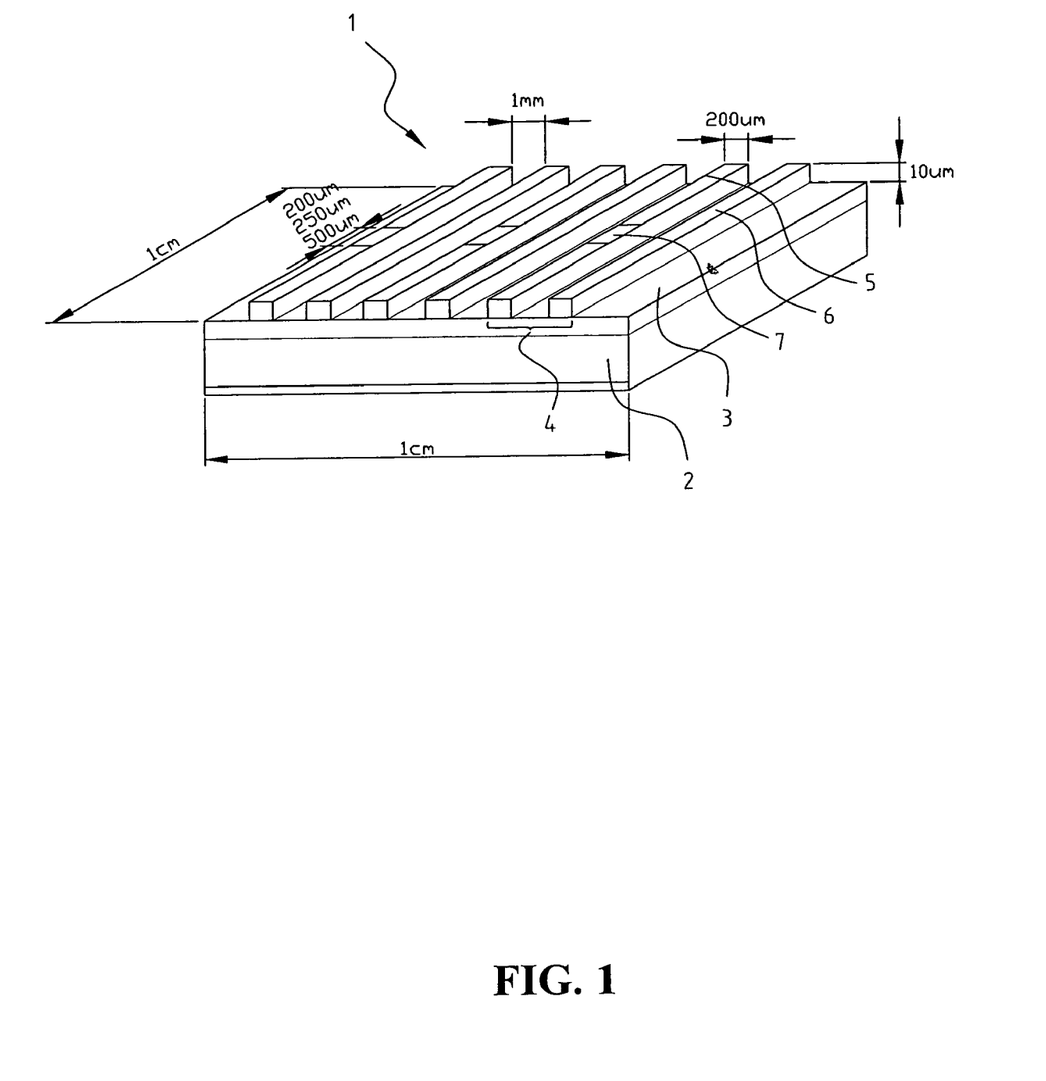
FIG. 1 is a schematic diagram illustrating an optical waveguide SPR sensor according to an embodiment of the present invention.

FIG. 1 is a schematic diagram illustrating an optical waveguide SPR sensor according to an embodiment of the present invention, in which there is shown a disposable sensor chip 1. According to an embodiment of the present invention, the disposable chip 1 includes a base 2, a bottom layer 3, at least one set of optical waveguide layers 4, and an SPR sensing film layer 7. The bottom layer 3 is disposed on the base 2, serving as an optical waveguide cover layer. The set of the optical waveguide layers 4 includes a measuring optical waveguide channel 5 and a reference optical waveguide channel 6. The SPR sensing film layer 7 is disposed on the measuring optical waveguide channel 5.

Second Embodiment

Figure 2:
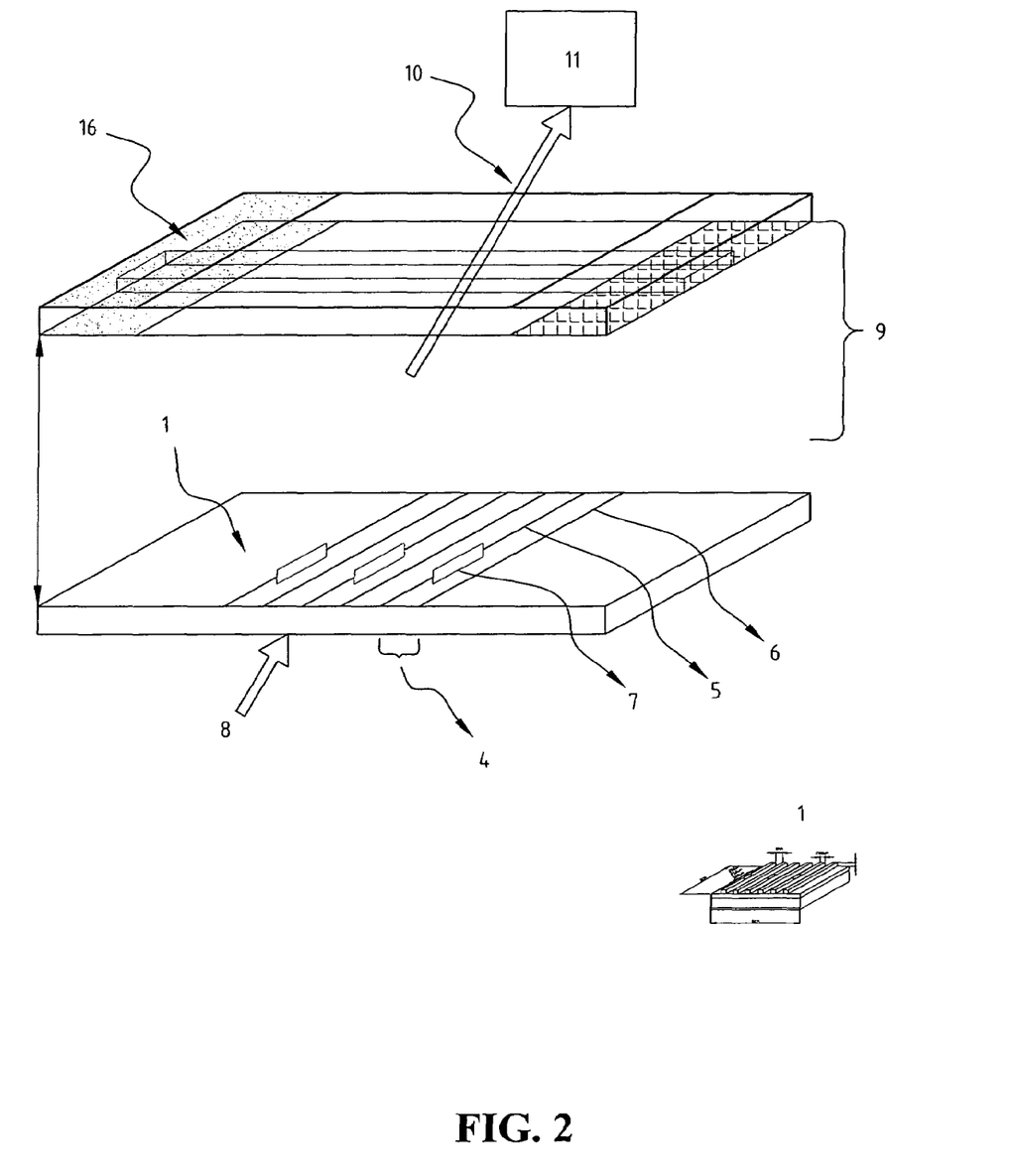
FIG. 2 is a schematic diagram illustrating an optical waveguide SPR sensor according to another embodiment of the present invention.

FIG. 2 is a schematic diagram illustrating an optical waveguide SPR sensor according to another embodiment of the present invention. According to the embodiment of the present invention, the SPR sensor further includes a flow conducting structure layer 9 disposed thereon. Samples or analyte can be conducted to the sensor chip 1 from one side of the sensor chip 1. When a light 8 enters the measuring optical waveguide channel 5 and the reference optical waveguide channel 6, the SPR sensing film layer 7 obtains a sensing signal 10 and transmits the sensing signal 10 to a spectrum analyzer 11 for a differential calculation and generating a spectrum thereby. According to an aspect of the embodiment, for convenience of operation and providing further protection to the sensor chip 1 and the flow conducting structure layer 9, the SPR sensor further includes two casings respectively over the flow conducting structure layer 9 and under the sensor chip 1. The two casings are adapted to engage one to another, and after engaged, the two casings are adapted for handheld operation.

Figure 3:
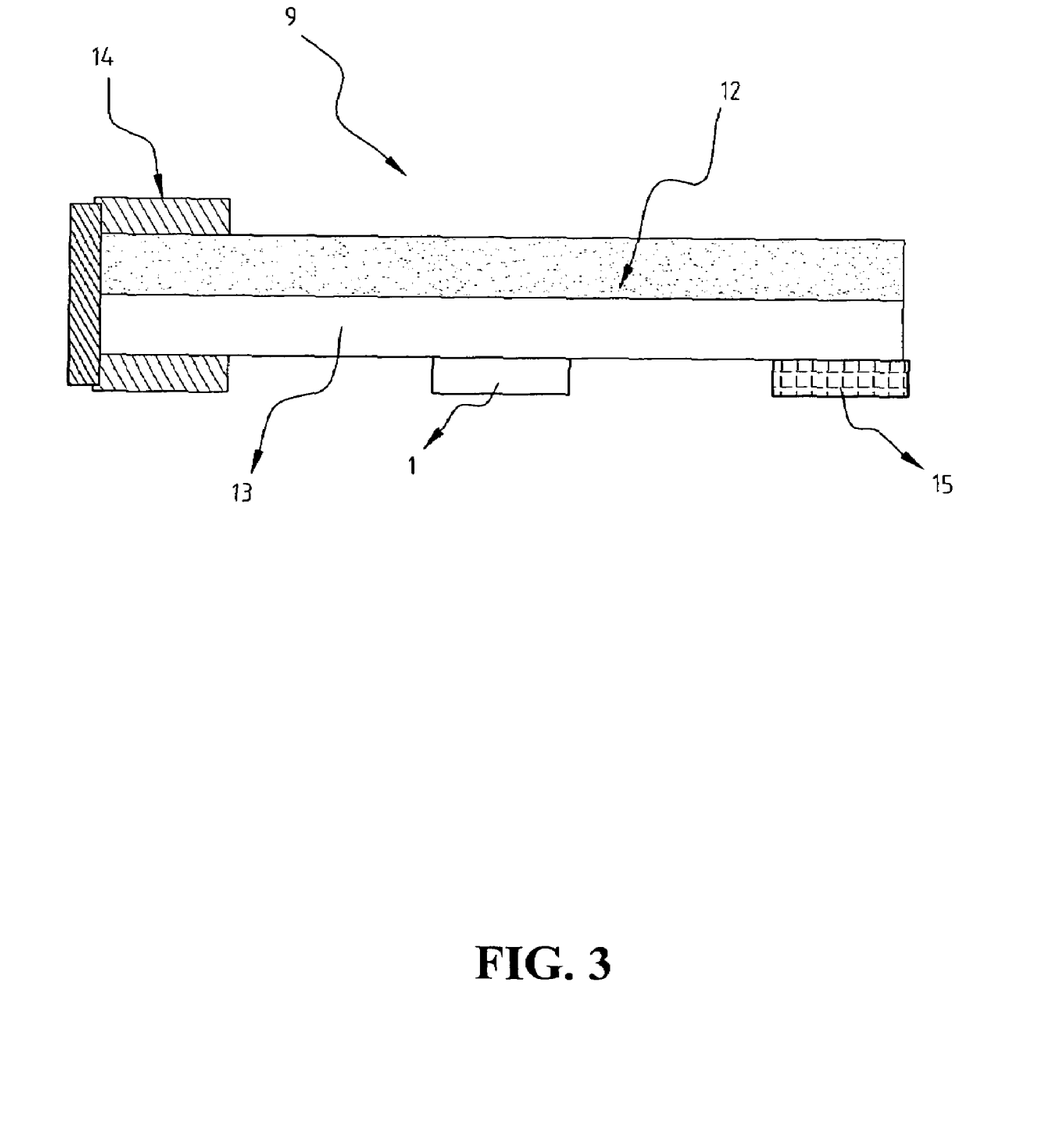
FIG. 3 is cross-sectional view of the flow conducting structure layer.

FIG. 3 is cross-sectional view of the flow conducting structure layer 9. Referring to FIG. 3, there is shown the flow conducting structure layer 9 including a substrate 12, a filter film layer 13, a sample loading pad 14, and an absorption pad 15. The substrate 12 is adapted for supporting other structures. The filter film layer 13 for example is made of nitrocellulose, and is disposed under the substrate 12 for filtering the sample conducted thereto. The sample loading pad 14 is disposed at one end of the flow conducting structure layer 9, and the absorption pad 15 is disposed at another end of the flow conducting structure layer 9 opposite to the sample loading pad 14 for absorbing excessive introduced sample. In operation, the sample is loaded to the sample loading pad 14. Then the filter film layer 13 filters to remove matters which may disturb the measurement. The sample is then conducted by a diffusion process through the filter film layer 13 to the sensor chip 1 for measurement. Excessive samples are absorbed by the absorption pad 15.

Third Embodiment

Figure 4:
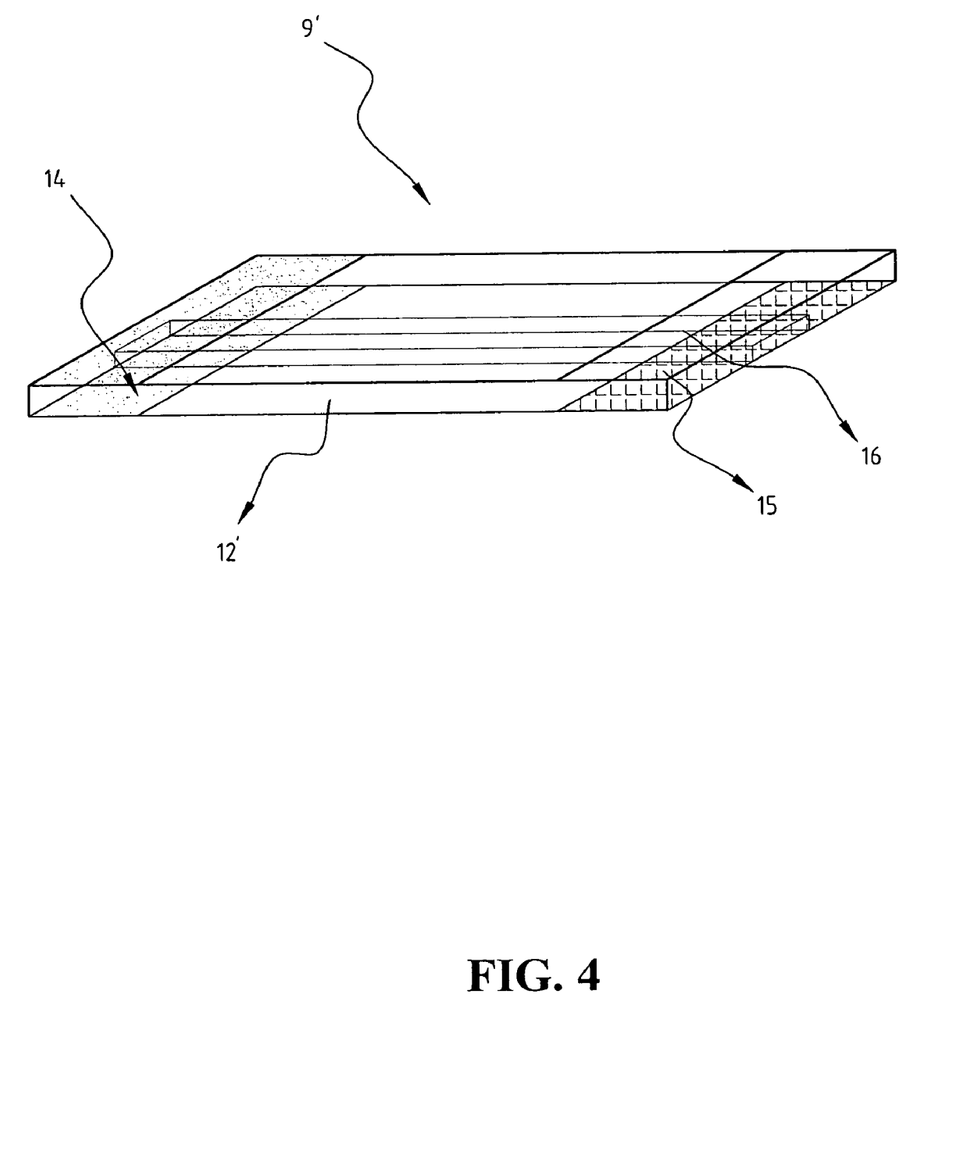
FIG. 4 is a schematic diagram illustrating the flow conducting structure layer according to another embodiment of the present invention.

FIG. 4 is a schematic diagram illustrating the flow conducting structure layer according to another embodiment of the present invention. Referring to FIG. 4, there is shown a flow conducting structure layer 9'. The flow conducting structure layer 9' includes a substrate 12' for supporting other structures thereof. There is configured a micrometer scale slot structure 16 at one side of the substrate 12' facing the optical waveguide layer 4 (not shown in this drawing). The slot structure 16 is adapted for conducting the sample. According to an aspect of the embodiment, a depth of the micrometer scale slot structure 16 preferably is from 10 μm to 500 μm, and is fabricated by a microlithography or optical etching process. The micrometer scale slot structure 16 serves as a capillary and is adapted for conducting liquid sample to the sensor chip 1. Further, there is disposed a sample loading pad 14 at one end of the flow conducting structure layer 9' for loading the liquid sample, and there is disposed a absorption pad 15 at an end of the flow conducting structure layer 9' opposite to the sample loading pad 14 for absorbing excessive samples. Furthermore, the flow conducting structure layer 9' may further include a filter film layer (not shown) included in the sample loading pad 14 or the micrometer slot structure 16 for filtering the liquid sample. The filter film layer can be made of nitrocellulose or cellulose acetate. The filter film layer can be configured by dissolving the nitrocellulose or cellulose acetate and then evenly coating the solution on the sample loading pad 14 or in the micrometer scale slot structure 16. In operation, the sample is loaded by the sample loading pad 14, and is then conducted by the micrometer scale slot structure 16 to the sensor chip 1 for measurement. Excessive samples are absorbed by the absorption pad 15.

Fourth Embodiment

Figure 5:
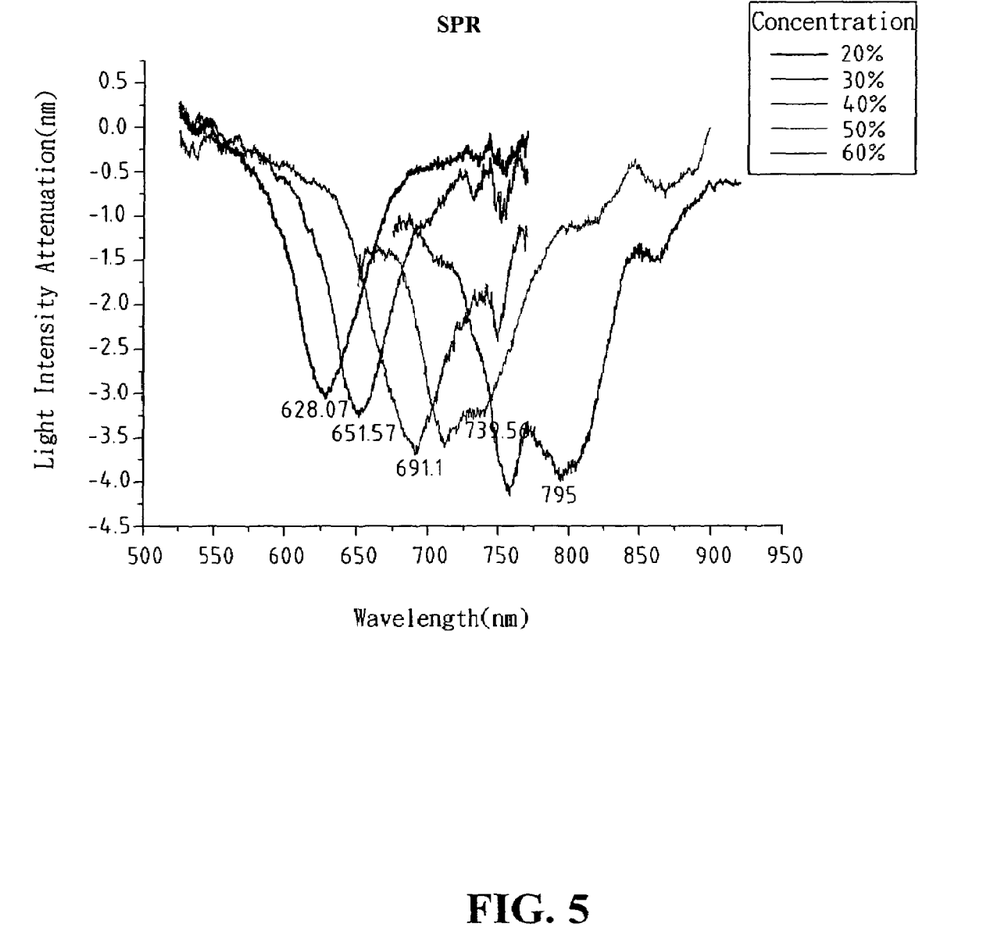
FIG. 5 is a diagram obtained by the optical waveguide SPR sensor shown in FIG. 2, in measuring glycerol aqueous solutions of different concentrations.

FIG. 5 is a diagram obtained by the optical waveguide SPR sensor shown in FIG. 2, in measuring glycerol aqueous solutions of different concentrations varying in the range of 20-60%. As shown in FIG. 5, a higher concentration of the glycerol aqueous solution corresponds to a longer characteristic wavelength at which light intensity sharply attenuates. Referring to FIG. 5, a relationship curve can be obtained from the measured characteristic wavelengths and the corresponding concentrations of the glycerol aqueous solutions. As such, a concentration of an analyte can also be obtained when its characteristic wavelength is measured and in accordance with the relationship curve. Therefore, the SPR sensor according to the present invention can be applied for measuring different concentrations of matters.

Fifth Embodiment

Figure 6:
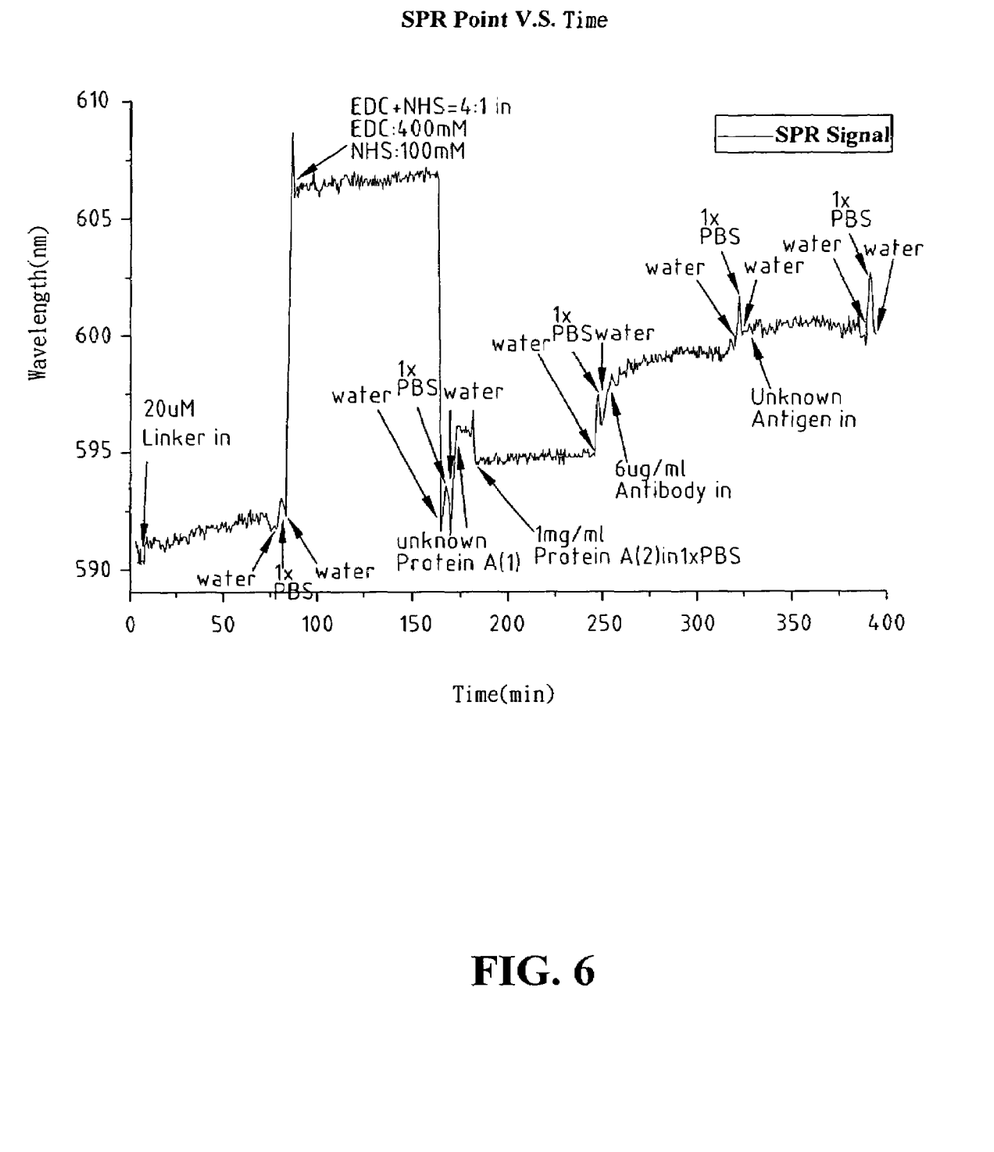
FIG. 6 is a diagram illustrating a measurement of the optical waveguide SPR sensor shown in FIG. 2, in which a gold (Au) film of the SPR sensing film layer is performed with a surface modification process.

FIG. 6 is a diagram illustrating a measurement of the optical waveguide SPR sensor shown in FIG. 2, in which a gold (Au) film of the SPR sensing film layer is performed with a surface modification process. In the embodiment, the gold film of the SPR sensing film layer of the SPR sensor of FIG. 2 has been surface modified. In a measuring operation, according to the embodiment, a 20 μM bridging molecule solution flows over a surface of the gold film; and then the gold film is washed with water and PBS buffer liquid; then a solution mixture of EDC and NHS with a mixing ratio of 4:1 flows over a surface of the sensing film layer for activating the same; then water is used to wash the surface; a protein A solution then flows over the surface of the sensing film layer and is fixed thereto; then water and PBS solution are again used for washing the surface; then a 6 μg/ml ALV-J monoclonal antibody solution flows over the surface of the sensing film layer; and then the surface is washed with water and PSB solution; and finally unknown antigen (analyte hereby) is introduced to flow over the surface of the sensing film layer. It can be concluded from the diagram shown in FIG. 6, the SPR sensor of the present invention is adapted to monitoring a variation of the surface of the sensing film layer according to the changes of the characteristic wavelengths.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An optical waveguide surface plasmon resonance (SPR) sensor, adapted for differential measurement, comprising:
   a base;
   a bottom layer; and
   at least one set of optical waveguide layers, the set of the optical waveguide layers comprising a measuring optical waveguide channel and a reference optical waveguide channel, wherein the measuring optical waveguide channel comprises an SPR sensing film layer, and the measuring optical waveguide channel and the reference optical waveguide channel are independently configured and substantially parallel one to another, and wherein the bottom layer has a refractive index higher than a refractive index of the optical waveguide layer.

2. The optical waveguide SPR sensor according to claim 1, wherein the base is made of a silicon wafer, a glass, or a macromolecule material.

3. The optical waveguide SPR sensor according to claim 1, wherein the bottom layer is made of a material selected from the group consisting of photoresist material, silicon dioxide, doped silicon dioxide, and macromolecule material.

4. The optical waveguide SPR sensor according to claim 1, wherein a thickness of the bottom layer is not less than 5 μm.

5. The optical waveguide SPR sensor according to claim 1, wherein the optical waveguide layer is made of a material selected from the group consisting of photoresist material, silicon dioxide, doped silicon dioxide, and macromolecule material.

6. The optical waveguide SPR sensor according to claim 1, wherein a thickness of the optical waveguide layer is not less than 10 μm.

7. The optical waveguide SPR sensor according to claim 1, wherein a distance between adjacent optical waveguide channels in the optical waveguide layer is from about 500 μm to about 5000 μm.

8. The optical waveguide SPR sensor according to claim 1, wherein a width of the optical waveguide channel is from 20 μm to about 500 μm.

9. The optical waveguide SPR sensor according to claim 1, wherein the SPR sensing film layer is a metal film, or an alloy film.

10. The optical waveguide SPR sensor according to claim 9, the SPR sensing film layer further comprises a biomolecule which can be combined with an analyte.

11. The optical waveguide SPR sensor according to claim 10, wherein the biomolecule is selected from the group consisting of nucleic acid, peptide, and protein.

12. The optical waveguide SPR sensor according to claim 1, wherein the SPR sensing film layer further comprises a plurality of layers of dielectric films.

13. The optical waveguide SPR sensor according to claim 1, further comprising a flow conducting structure layer disposed on the optical waveguide layer.

14. The optical waveguide SPR sensor according to claim 13, wherein the flow conducting structure layer comprises:
    a substrate, serving as a supporter supporting other structures;
    a filter film layer, disposed under the substrate for filtering and conducting a sample;
    a sample loading pad, disposed at an end of the flow conducting structure layer for loading the sample; and
    an absorption pad, disposed at another end of the flow conducting structure layer opposite to the sample loading pad for absorbing excessive sample.

15. The optical waveguide SPR sensor according to claim 13, wherein the flow conducting structure layer comprises:
    a substrate, serving as a supporter supporting other structures;
    a micrometer scale slot structure, disposed at a side of the substrate facing the optical waveguide layer for conducting a sample therein;
    a sample loading pad, disposed at an end of the flow conducting structure layer for loading and filtering the sample;
    an absorption pad, disposed at another end of the flow conducting structure layer opposite to the sample loading pad for absorbing excessive sample; and
    a filter film layer, disposed at an area of the sample loading pad.

16. The optical waveguide SPR sensor according to claim 13, wherein the flow conducting structure layer comprises:
    a substrate, serving as a supporter supporting other structures;
    a micrometer scale slot structure, disposed under the substrate for conducting and filtering a sample;
    a sample loading pad, disposed at an end of the flow conducting structure layer for loading the sample;
    an absorption pad, disposed at another end of the flow conducting structure layer opposite to the sample loading pad for absorbing excessive sample; and
    a filter film layer, disposed in the micrometer scale slot structure.

17. The optical waveguide SPR sensor according to claim 14, wherein the filter film layer is made of nitrocellulose or cellulose acetate.

18. The optical waveguide SPR sensor according to claim 15, wherein the filter film layer is made of nitrocellulose or cellulose acetate.

19. The optical waveguide SPR sensor according to claim 16, wherein the filter film layer is made of nitrocellulose or cellulose acetate.

20. The optical waveguide SPR sensor according to claim 17, wherein a refractive index of the flow conducting structure layer is from about 1.33 to about 1.35.

21. The optical waveguide SPR sensor according to claim 18, wherein a refractive index of the flow conducting structure layer is from about 1.33 to about 1.35.

22. The optical waveguide SPR sensor according to claim 19, wherein a refractive index of the flow conducting structure layer is from about 1.33 to about 1.35.

23. The optical waveguide SPR sensor according to claim 1, wherein the optical waveguide SPR sensor is disposable.

* * * * *